United States Patent [19]

Kammann et al.

[11] Patent Number: 5,442,287
[45] Date of Patent: Aug. 15, 1995

[54] METHOD AND APPARATUS FOR DETECTING MAGNETIC DISCONTINUITIES BY INDUCING A MAGNETIC FIELD IN A MAGNETIZABLE SAMPLE

[75] Inventors: Reinhold Kammann, Wienhausen; Helmut Knapwost; Manfred Worms, both of Nienhagen; Helgo Deeg, Winsen, all of Germany

[73] Assignee: Tuboscope Vetco (Deutschland) GmbH, Germany

[21] Appl. No.: 235,636

[22] Filed: Apr. 29, 1994

[30] Foreign Application Priority Data

May 3, 1993 [EP] European Pat. Off. .......... 93107122

[51] Int. Cl.⁶ .................. G01N 27/82; G01N 27/83
[52] U.S. Cl. .................. 324/242; 324/235; 324/262
[58] Field of Search ............ 324/232, 235, 240–243, 324/262

[56] References Cited

FOREIGN PATENT DOCUMENTS

0238209B1 9/1987 European Pat. Off. .
0238209A2 9/1987 European Pat. Off. .
0238209A3 9/1987 European Pat. Off. .

Primary Examiner—Gerard R. Strecker
Attorney, Agent, or Firm—Finnegan, Henderson, Farabow, Garrett & Dunner

[57] ABSTRACT

A testing method and apparatus detects magnetic discontinuities in a sample of magnetizable material. The apparatus may include an electric motor, a transmission, driven transport wheels, and non-driven transport wheels. Further, the apparatus includes a magnetizing device for inducing a magnetic field in the sample. A sensor unit detects magnetic stray flux from the magnetic field induced in the sample and converts the detected magnetic stray flux into a signal for processing by a signal processor.

19 Claims, 4 Drawing Sheets

METHOD AND APPARATUS FOR DETECTING MAGNETIC DISCONTINUITIES BY INDUCING A MAGNETIC FIELD IN A MAGNETIZABLE SAMPLE

BACKGROUND OF THE INVENTION

1. Field of the Invention

The present invention is directed to a testing method and apparatus. More particularly, the present invention is directed to a method and apparatus for detecting magnetic discontinuities in a sample of magnetizable material.

2. Description of the Related Art

Methods and apparatus are known for generally detecting magnetic discontinuities. For example, a conventional apparatus is disclosed in European Patent, RP 0 238 209 B1.

However, there is a need for a method and apparatus for the reliable detection and location of magnetic discontinuities in samples, such as flat floor plates of large containers or tanks, so as to accurately determine the dimensions of the detected discontinuities, including the depth. Further, it is desirable to locate the discontinuities when they are found on the side of the sample opposite to the testing apparatus.

SUMMARY OF INVENTION

Accordingly, the present invention is directed to a testing method and apparatus that substantially obviates one or more of the problems due to limitations and disadvantages of the related art.

To achieve these and other advantages and in accordance with the purpose of the invention, as embodied and broadly described, the invention includes a method of detecting magnetic discontinuities in a sample of magnetizable material, comprising the steps of inducing a magnetic field into the sample; detecting magnetic stray flux values close to the surface of the sample resulting from the magnetic field in the sample using sensors; transforming the determined values into electric voltage signals by movement of a magnetic field induction and sensor unit along a preselected path over the sample; analyzing the electrical voltage signals corresponding to the magnetic stray flux in a signal processor and outputting a signal from the signal processor representing the analysis; amplifying the electrical voltage signals provided by the sensor in a programmable amplifier with high common mode rejection ratio and automatic drift control; filtering, in a signal valuation step, the output signals from the amplifier in a frequency dependent evaluation with higher weighting of the signals caused by the low frequency stray flux from discontinuities of shallow depth; and providing the filtered signals in a time-related fashion as an input signal to a peak value calculation and holding step. The output signal corresponds to the input signal value during a rising amplitude of the input signal, and a last measured maximum value of the amplitude is held for a preselected period of time and is thereafter deleted during a falling amplitude of the input signal, unless the input signal reaches an amplitude value which exceeds the held maximum value during the holding and deleting step, in which case the output signal is updated and the holding procedure is cancelled.

In another aspect, the invention includes an apparatus for detecting magnetic discontinuities in a sample of magnetizable material, comprising a carriage movable along a predetermined path on the sample; sensors for detecting magnetic stray flux close to the surface of the sample resulting from a magnetic field and detected discontinuities; a signal processor; and means for optically displaying and storing test results for further evaluation. The signal processor comprises a programmable amplifying module for amplifying the electrical signals from the sensors corresponding to the magnetic stray flux from the sample with high common mode rejection ratio and automatic drift control, a signal valuation module for filtering the amplified signals from the amplifying module using a frequency dependent evaluation where more weight is given to signals originating from low frequency stray flux in discontinuities of shallow depth, and a peak value calculating and holding module for preparing, in time-dependent fashion, the filtered signals from the signal valuation module so that the output signal corresponds to the input value during a rising amplitude of the input signal and a latest measured maximum value is held for a preselected period of time and thereafter deleted during a decreasing amplitude of the input signal, unless the input signal reaches a value exceeding the held maximum value during the holding and deletion phase, in which case the output signal corresponds to the input signal without loss of amplitude and the holding step is cancelled.

The method and apparatus according to the invention assures a high degree of reliability in the detection of discontinuities and accuracy in the determination of data concerning the extent of the discontinuities. The different weighting of the signals is based on the frequency contents, which creates a balance with an approximate linearizing action on the relation of signal height (signal amplitude) and depth of discontinuities. The peak value formation and holding guarantees a definite detection and determination also of signals of low frequency contents, thereby maintaining the linearizing action achieved in the signal evaluation stage.

The apparatus of the present invention provides a simple basic structure for optimizing the data accuracy, while allowing adjustment to the specific inspection conditions. The special structure of the sensor holders in the apparatus promotes a uniform and disturbance-free detection also of smaller magnetic stray flux values, whereby the sensor holders exhibit good characteristics even when the apparatus is moving over an uneven path.

It is to be understood that both the foregoing general description and the following detailed description are exemplary and explanatory and are intended to provide further explanation of the invention as claimed.

BRIEF DESCRIPTION OF DRAWINGS

The accompanying drawings, which are incorporated in and constitute a part of this specification, illustrate a preferred embodiment of the invention and, together with the description, serve to explain the objects, advantages, and principles of the invention.

In the drawings.

DETAILED DESCRIPTION

Reference will now be made in detail to the present preferred embodiment of the invention, an example of which is illustrated in the accompanying drawings.

Figure 1:
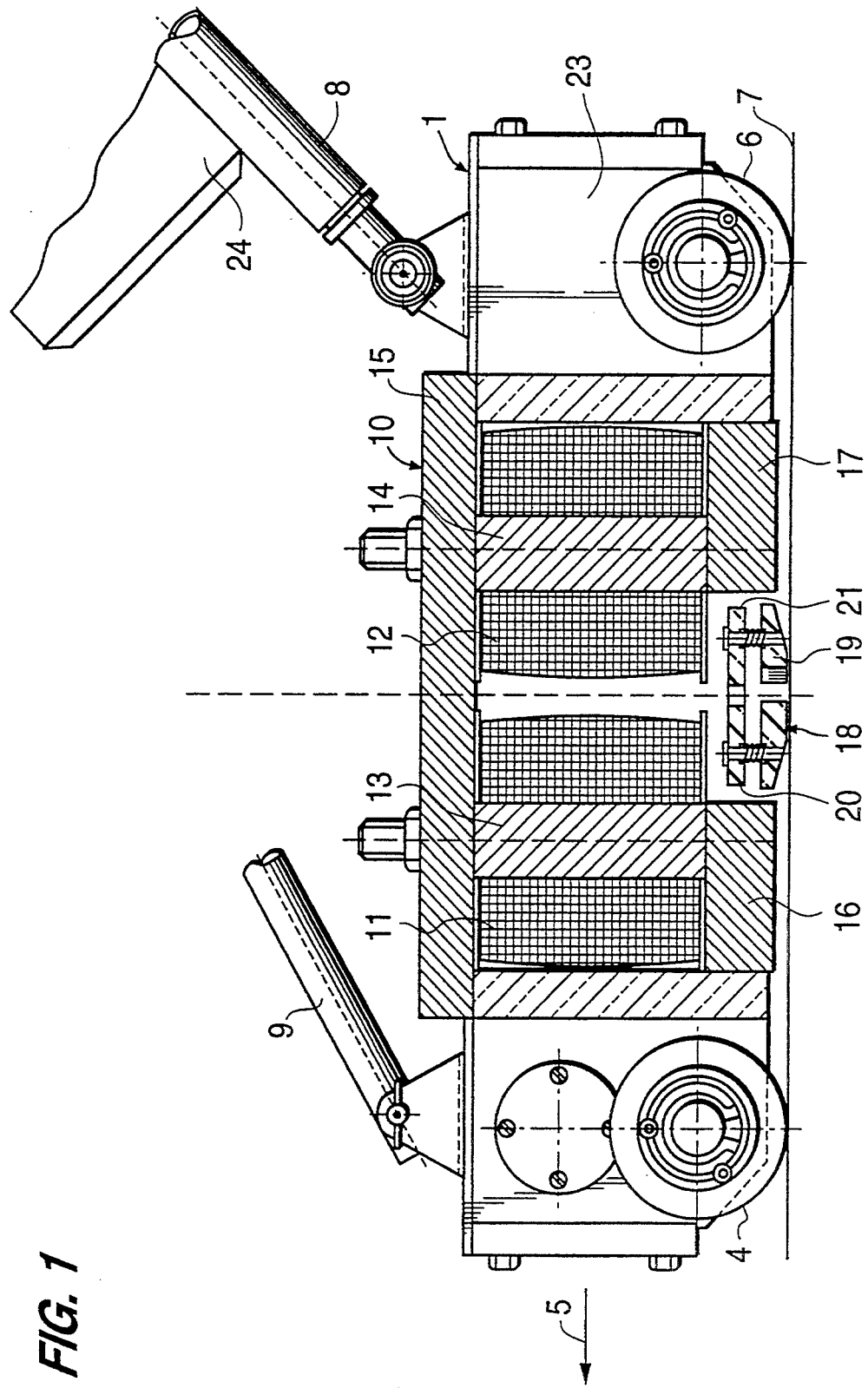
FIG. 1 is a side view of a testing apparatus according to an embodiment of the present invention.
Figure 2:
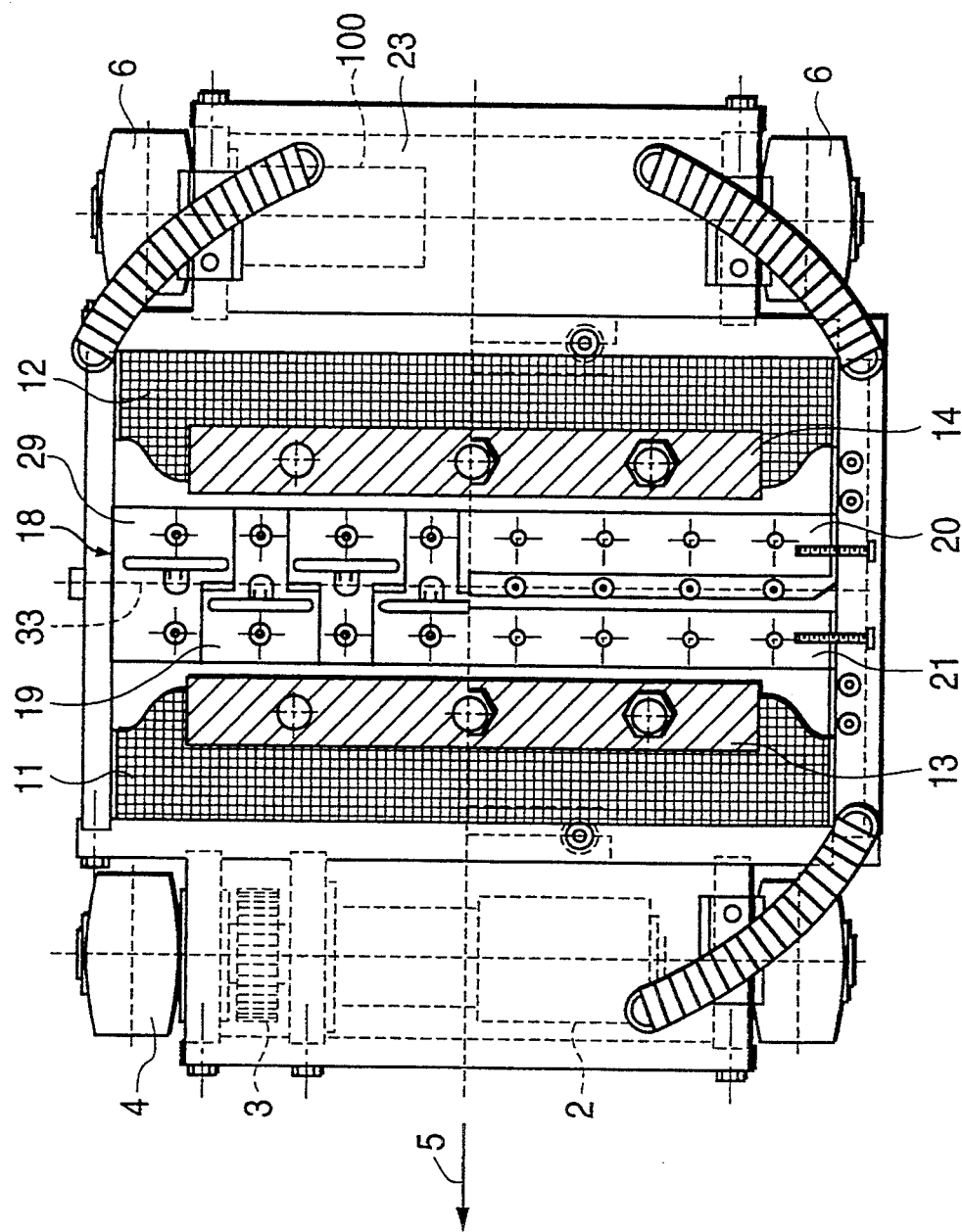
FIG. 2 is a top view of the apparatus shown in FIG. 1.

FIGS. 1 and 2 show a side view and top view, respectively, of a preferred embodiment of the present invention. The testing apparatus detects magnetic discontinuities and irregularities in a sample of magnetizable material by inspecting large areas and essentially flat samples, such as the floor plates of a large container or tank.

As shown in FIGS. 1 and 2, the testing apparatus, which is movable along a preselected path on tank floor 7 in transport direction 5, includes a hand guidable carriage 1, electric motor 2, transmission 3, driven transport wheel 4, and non-driven transport wheels 6. Electric motor 2 drives driven transport wheels 4 via transmission 3, with non-driven wheels 6 serving as rear wheels. Guidance system 8 is provided to direct carriage 1. The slope of guidance system 8 is adjustable with a tie-rod 9 of adjustable length Further, the guidance system 8 can support additional components of the testing apparatus, such as, for example, an optical display device for providing information to an operator.

Further, the testing apparatus comprises a magnetizing device 10 for inducing a magnetic field in the sample to be tested, in this case, tank floor 7. The magnetizing device 10 comprises at least two electromagnets, the coils of which are denoted 11 and 12, respectively, and the magnet and coil core of which are denoted 13 and 14, respectively. A magnetic return path plate above the magnets is denoted 15 and the pole shoes 16 and 17. The pole shoes extend crossways to the driving direction 5 horizontally and close to the tank floor 7 and have a length which essentially corresponds to the total width of the apparatus.

In the space between the pole shoes 16, 17, a sensor unit 18 is arranged comprising a number of sensor holders 19, which are suspended on carrier bars 20, 21, and is described in greater detail below.

The testing apparatus, which can be connected to a power supply via a cable, also includes sensor unit 18 and a signal processor 22, which is described in detail below in connection with FIG. 4. The signal processor 22 may, for example, be arranged in compartment 23 of the testing apparatus or in a housing 24 mounted on the guidance system 8 as shown in FIG. 1. In addition, as mentioned above, an optical display device can also be directly connected to and carried by the apparatus in, for example, compartment 23 or housing 24. Other means for evaluating and storing collected data may also be carried by the guidance system 8, or arranged stationary at a suitable distance from and connected to the apparatus with suitable cables. For the sake of completeness, it should be mentioned that the electric part of the apparatus of the present invention comprises connection leads, switches for activating the aggregates, control means, and attenuators.

Figure 3:
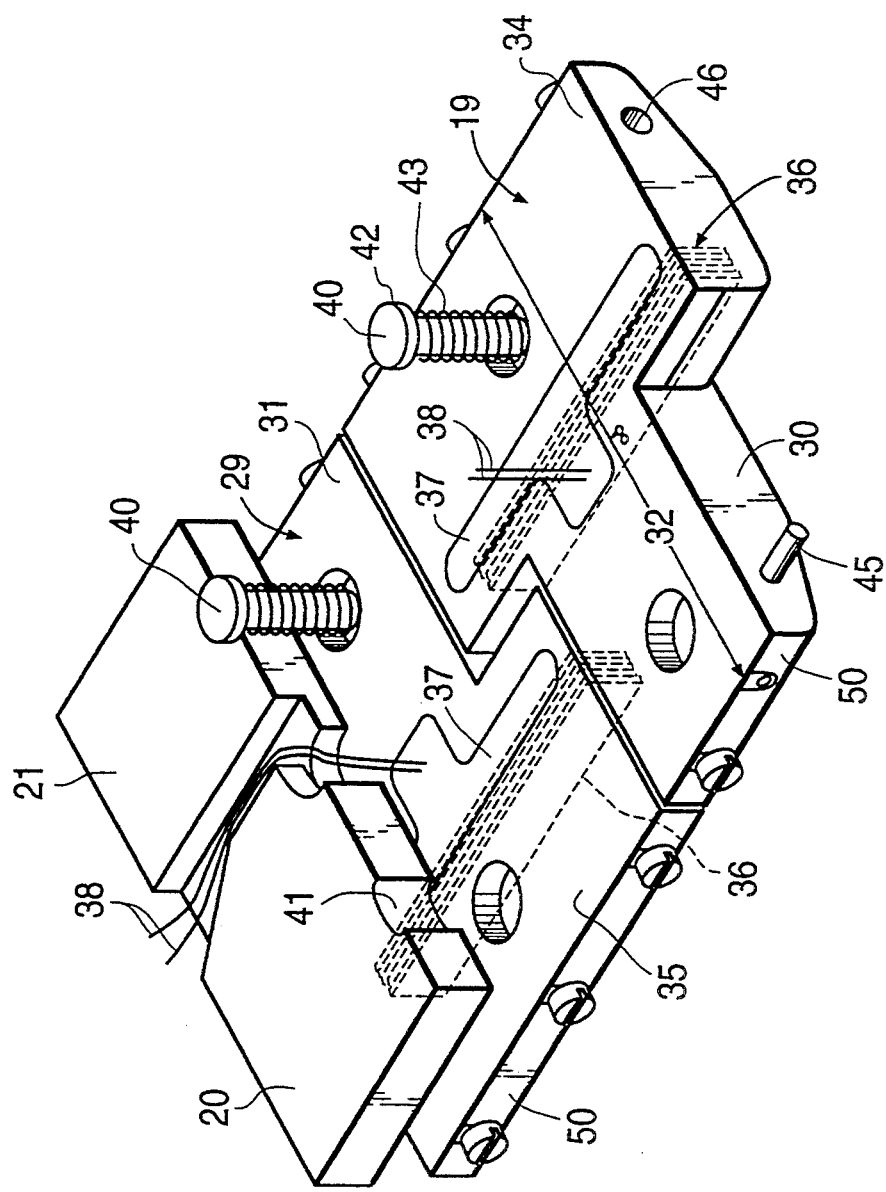
FIG. 3 is a perspective view of the sensor holders and their suspension according to the present invention.

As is shown in FIGS. 2 and 3, the sensor unit 18 comprises T-shaped sensor holders 19, which form the main part of the sensor unit 18, and L-shaped sensor holders 29 arranged at the ends of the sensor unit 18. The T-shaped and L-shaped sensor holders 19, 29, respectively, each have sides 30 and 31 directed parallel to the transport direction 5 a total depth 32, which is equivalent to the total width of the sensor unit 18 measured in the transport direction 5. Sensor holder 19, 29 also include head pieces 34, 35, respectively. Together, the sensor holders 19, 29 form a sensor unit 18 of rule-like shape and rectangular outline, wherein the alternately aligned sensor holders 19 extend in a comb-like interlocking arrangement, in and against the transport direction, over the longitudinal central axis 33 of the sensor unit 18, which axis extends crossways to the transport direction 5 of the carriage 1.

Besides T-shaped and L-shaped sensor holders 19, 29, sensor holders of other shapes may also be used. For example, sensor holders of triangular shape may be used, where the height of the triangle is equivalent to the total width of the sensor unit 18. Also the shape of a sensor holder may be used to form a sensor unit having a sensor-rule or rectangular outline, where central sensor holders are in the shape of isosceles triangles and sensor holders in the shape of adapted straight-angled triangles are arranged as supplementing pieces at the ends of the sensor unit.

As shown in FIG. 3, head pieces 34, 35 of the sensor holders 19, 29, respectively, support sensors 36, which preferably are designed as rod shaped vertical coils, but which may also be designed as Hall-sensors or any other suitable sensors. Vertical coils have the advantage that they measure differential stray flux differences. Preferably, the sensors 36 are arranged in conforming recesses in the sensor holders 19, 29 and are fixed and protected by being moulded in a sealing compound from which only the connection leads 38 extend outwards. The sensors 36 are, corresponding to the alternating direction of the sensor holders 19, arranged in two crossways to the transport direction 5 of the carriage 1 and parallel to the direction of the pole shoes 16, 17 extending rows. The sensors 36 in one of the rows are arranged with an interspace (gap) in relation to the sensors 36 in the other row and overlap each other mutually at their ends. The total overlap of the sensors 36 in the sensor unit 18 preferably is at least 10%.

The sensor holders 19, 29 are attached to the carriage 1 in a way which permits a restricted vertical movement. For this purpose, they are provided with upwards extending guidance pins 40 extending through and engaging guidance openings 41 in the carrier bars 20, 21, which are secured to the carriage 1. The guidance pins 40 extend with their heads 42 over the respective guidance bore 41 and thereby limit the lower end position of the sensor holders 19, 29. The sensor holders 19, 29 are loaded with compression springs 43, which preferably consist of coil pressure springs which surround the guidance pins 40 and rest against the sensor holders on one side and against the carrier bars 20, 21 on the other side.

The sensor holders 19, 29 are, furthermore, interconnected to each other by hinges. For this purpose, the parts 30, 31 of the sensor holders 19, 29, respectively, which are positioned parallel to the transport direction 5 of the carriage 1, are provided with hinge pins 45. The pills 45 are positioned parallel to the central longitudinal axis 33 of the sensor unit 18 and extend with clearance into and engage aligned opposite bearing bores 46 in the head parts 34, 35 of neighboring sensor holders 19, 29.

The vertical movability of the sensor holders 19, 29 provides, in conjunction with the flexible linkage of the sensor holders, a structure that produces a good conformity to the areas of the tank floor 7 over which the sensor unit travels and guarantees effective movement over high and abrupt uneven portions, such as welding seams between the floor plates. The extension of all sensor holders 19, 29 over the total width of the sensor unit 18 provides for relatively small position changes of the sensors 36 while traveling over uneven portions, and provides for position stabilization of the sensor holders 19, 29 with the sensor unit 18 so that accurate test data may be obtained.

The bottom of the sensor holders 19, 29 are covered by a removably secured, e.g., screwed on, wear resistant slide plate 50, which acts as an exchangeable wear part so that the sensor holders 19, 29 and sensors 36 are protected from wear.

Figure 4:
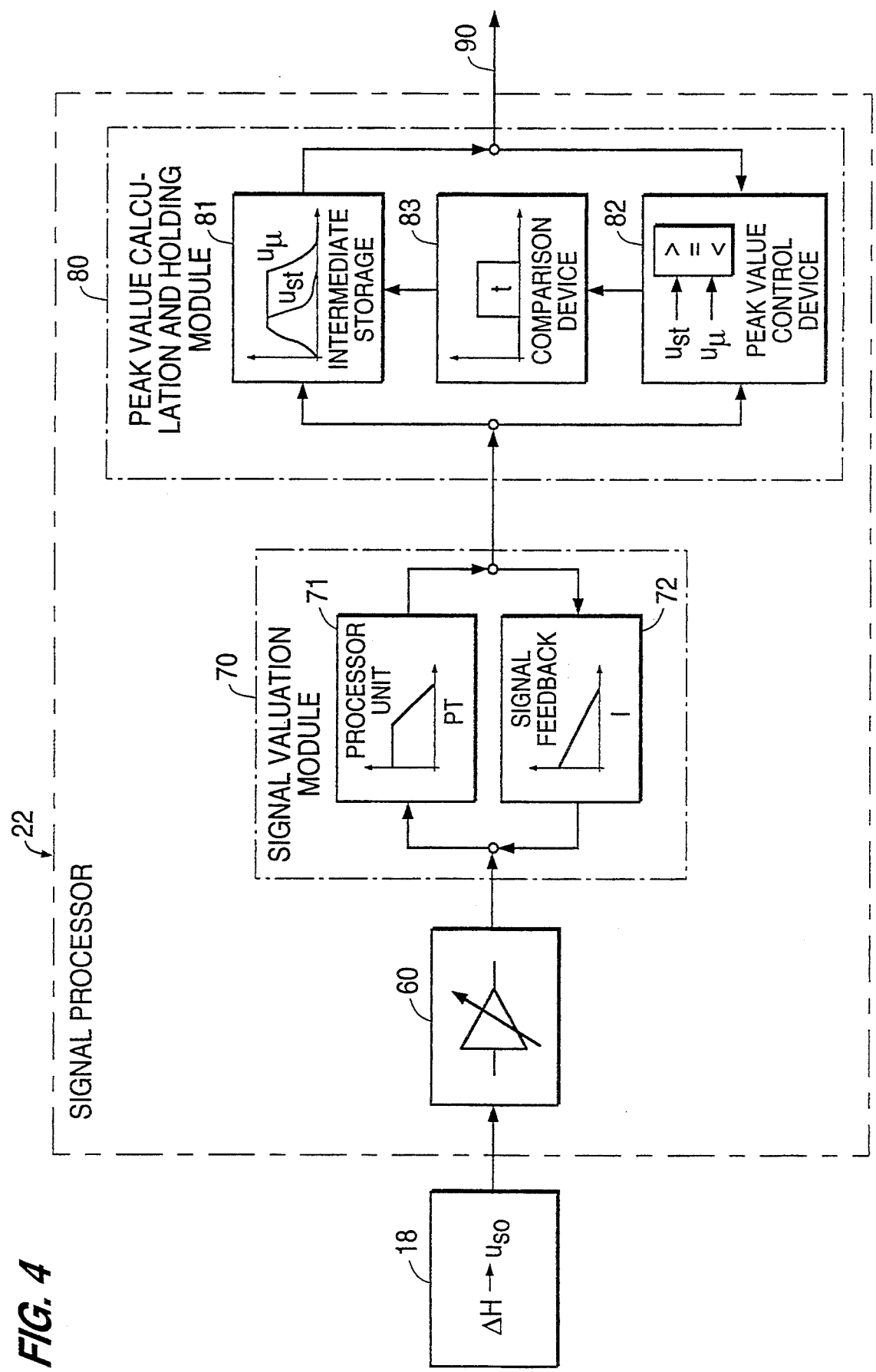
FIG. 4 is a block diagram of the signal processor of the present invention.

FIG. 4 shows a block diagram of signal processor 22 comprising a programmable amplifier module 60. Signals are provided from the sensors 36 as part of the sensor unit 18, detected as stray flux $\Delta H$, and formed into voltage signals $u_{so}$ with proportional amplitude to $\Delta H$, to the amplifier module 60, which amplifies the signals up to 120 dB. At the same time, the amplifier module 60 surveys the function of the sensors 36. Furthermore, the signal processor 22 includes a signal valuation module 70, that includes a processor unit 71 with $PT_1/PT_2$-transmission characteristics (time delay second order) and a signal feedback 72 with integral character I. The total signal valuation module 70 has a differential-proportional-integral character. In the signal valuation stage, a frequency dependent signal evaluation adjusted to the expected signal range takes place, whereby the output signals of the amplifier module 16 by filtering are subjected to an evaluation with higher weighting of the signals originating from lower frequency stray flux of discontinuities of low depth with the consequence of a formation of an at least almost linear relation between the output signals from the signal valuation module 70 and the depth measurements of the relating discontinuities.

Finally, the signal processor 22 of the testing apparatus includes a peak value calculation and holding module 80 with an intermediate storage 81 with the input signal $u_{s1}$ and the output signal $u_p$, a peak value control device 82, and a comparison device 83. This module 80 refines the output signals of the signal valuation module 70 time dependently in a way that, with a rising amplitude of the input signal $u_{s1}$, the output signal $u_p$ follows the input signal $u_{s1}$ with the input value, and with a steady or falling amplitude of the input signal, the latest measured maximum value is held for a preselected time t. After the preselected period of time t has elapsed, the maximum value is deleted, if the input signal does not take on an amplitude value that exceeds the held maximum value during the holding or following deleting stage. In that case, the output signal will follow the input signal without amplitude loss so that the linearizing system achieved in the signal valuation module 70 is maintained throughout.

The signals, processed in that way in the signal processor 22, can be fed without loss of amplitude to the respective intended means for optical and, if necessary, acoustic signal display, as shown by arrow 90 in FIG. 4. At the same time, the output signal of the signal processor 22 can be fed into systems to be saved for further evaluation. An example of signal processor 22 is a computer system programmed to allow a graphical display of the distribution of discontinuities in the sample, according to dimension and depth.

The operation of the signal processor 22 will now be described. The stray flux signals continuously measured by the sensors 36 are transferred into voltage signals that are amplified in the amplifier module 60 with high common mode rejection ratio and automatic drift control. The preamplifier stage with a maximum gain of 120 dB can be programmed according to the grade of amplification, to thereby consider optically the special condition of a respective sample. The bandwidth of the amplifier module 60 is 0.1 to 300 Hz, which may be adjusted to special sample condition by programming.

The output signal of the amplifier stage is subjected to a frequency dependent evaluation by filtering at the signal valuation stage formed by the signal valuation module 70, where signals originating from the low frequency stray flux of discontinuities of low depth will be weighted higher than signals that originate from discontinuities of low depth that cause a low stray flux, but are higher in the frequency spectrum. The signals linearized in that way now are subjected to a time dependant refinement in the peak value calculation and holding stage of the module 80, during which the input signals are fed into an intermediate storage, as long as input signals with rising amplitude are concerned. When input signals are steady or have a falling amplitude, the output signal follows the input signal. Amplitudes are held at the momentary peak value at this moment for a preselected period of time so that shorter signals also get reliably recorded and are not missed. If, during this holding state, no input signals are greater than the peak value calculation, the latest held peak value is deleted after the preselected time passes. If, during the holding state and following the deleting phase, another input signal occurs whose amplitude exceeds the held or momentary peak value, the holding process will be cancelled so that the output signal can follow the input signal free of amplitude loss and can fed to the following signal display and/or documentation stage.

For the detection of magnetic discontinuities in a sample, namely tank floor 7, the testing apparatus in operational mode is moved along a preselectable path over the tank floor 7, where an optoelectrical distance transducer, which is preferably placed onto the axis of the non-driven wheels for avoiding false values caused by slip, supplies exact position data. Through suitable power supplies connected to the electromagnets 11, 13, and 12, 14, respectively, the induced field can be adjusted to the respective requirements as they occur based on the particularities of the sample, such as plate thickness, to optimize the accuracy of the detected data. For additional optimizing, the distance of the pole shoes 16, 17 to the surface of the sample is adjustable by, for example, adjusting the height of the transport wheel shafts relative to the carriage 1.

The testing method according to the invention is in its use not limited to the particular samples described herein, but can generally be used with any magnetizable samples, such as walls of pipes. This is also applicable for the above-described apparatus, though the disclosed embodiment is optimized for use on samples having even surfaces. It is understood that one skilled in the art could modify the disclosed apparatus for use on samples that do not have even surfaces.

It will be apparent to those skilled in the art that various modifications and variations can be made in the testing method and apparatus of the present invention without departing from the spirit or scope of the invention. Thus, it is intended that the present invention cover the modifications and variations of this invention provided they come within the scope of the appended claims and their equivalents.

What is claimed is:

1. A method of detecting magnetic discontinuities in a sample of magnetizable material, comprising the steps of:
   inducing a magnetic field into the sample;
   detecting magnetic stray flux values close to the surface of the sample resulting from the magnetic field in the sample using sensors;
   transforming the detected values into electric voltage signals;
   amplifying the electrical voltage signals in a programmable amplifier with high common mode rejection ratio and automatic drift control;
   filtering the amplified electric voltage signals from the amplifier in a frequency dependent evaluation and providing higher weighting of the signals caused by the low frequency stray flux from discontinuities of shallow depth; and
   providing the filtered signals in a time-related fashion as an input signal to a peak value calculation and holding step to produce an output signal corresponding to the input signal value during a rising amplitude of the input signal,
   wherein a last measured maximum value of the amplitude is held in memory for a preselected period of time and is thereafter deleted during a falling amplitude of the input signal, unless the input signal reaches an amplitude value which exceeds the held maximum value during the holding and deleting step, in which case the output signal is updated and the holding procedure is cancelled.

2. A method according to claim 1, wherein operation control of the sensors is performed in the amplifying step.

3. A method according to claim 1, wherein a control circuit with differential-proportional-integral character is used in the signal valuation step for signal valuation.

4. A method according to claim 1, wherein, for holding the peak value, the input signals in the peak value calculation and holding step are loaded into an intermediate storage following rising of the input signals, and the input and output signals are compared with each other on-line, and
   wherein the output signal is released to follow the input signal without loss of amplitude as soon as, in the holding or in deleting step, the value of the input signal exceeds the value of the output signal.

5. An apparatus for detecting magnetic discontinuities in a sample of magnetizable material, comprising:
   a magnetizing device for inducing a magnetic field in the sample of magnetizable material,
   sensors for detecting magnetic stray flux close to the surface of the sample resulting from the induced magnetic field and detected discontinuities and outputting electrical signals in accordance with the detected magnetic stray flux;
   a signal processor for processing the electrical signals to obtain test results; and
   means for optically displaying and storing the test results,
   said signal processor comprising:
      a programmable amplifying module for amplifying the electrical signals from the sensors corresponding to the magnetic stray flux from the sample with high common mode rejection ratio and automatic drift control,
      a signal valuation module for filtering the amplified signals from the amplifying module using a frequency dependent evaluation and providing more weight to signals originating from low frequency stray flux in discontinuities of shallow depth than signals originating from high frequency stray flux, and
      a peak value calculating and holding module for receiving the filtered signals from the signal valuation module as input signals and outputting an output signal which corresponds to a value of the input signal during a rising amplitude of the input signal and a latest measured maximum value is held in memory for a preselected period of time and thereafter deleted during a decreasing amplitude of the input signal, unless the input signal reaches a value exceeding the held maximum value during the holding and deletion phase, in which case the output signal corresponds to the input signal without loss of amplitude and the holding step is cancelled.

6. The apparatus according to claim 5, wherein the magnetizing device comprises electromagnets.

7. The apparatus according to claim 5, wherein said sensors comprise vertical coils arranged in sensor holders.

8. The apparatus according to claim 6, wherein the sensors are arranged in two rows running crossway to a driving direction of the carriage and parallel to a direction of pole shoes of the electromagnets.

9. The apparatus according to claim 7, wherein said sensor holders are attached to the carriage with restricted vertical mobility.

10. The apparatus according to claim 7, wherein each sensor holder is pre-loaded with a compression spring.

11. The apparatus according to claim 7, wherein the sensor holders together form a rule-shaped sensor unit of rectangular outline, and the sensor holders extend, comblike alternating in and against a driving direction, across the longitudinal center axis of the sensor unit, the axis extending crossways to the driving direction of the carriage.

12. The apparatus according to claim 7, wherein the sensor holders are T-shaped and have legs which extend parallel to a driving direction of tile carriage and which exhibit a total depth equivalent to a total width of the sensor unit.

13. The apparatus according to claim 7, wherein all the sensor holders are flexibly linked to each other.

14. The apparatus according to claim 13, wherein the sensor holders have legs which are positioned parallel to a driving direction of the carriage are provided with hinge pins which are arranged parallel to a longitudinal central axis of the sensor unit close to the end of said legs, said pins meshing into aligned opposite bearing bores in head pieces of neighboring sensor holders.

15. The apparatus according to claim 14, wherein the hinge pins fit into opposite bores with a suitable clearance.

16. The apparatus according to claim 7, wherein L-shaped sensor holders are arranged at ends of the sensor unit, said L-shaped sensor holders having sides parallel to a driving direction with a total depth equivalent to a total width of the sensor unit.

17. The apparatus according to claim 8, wherein the sensors in one of the rows are arranged with interstices and staggered in relation to the sensors in the other row, said sensors mutually overlapping each other at their ends.

18. The apparatus according to claim 17, wherein the sensors mutually overlap one another by at least 10%.

19. The apparatus according to claim 7, wherein the sensor holders are covered at a lower side by a connectably attached wear resistant slide plate.

* * * * *